United States Patent [19]

Hayashi et al.

[11] Patent Number: 5,013,845
[45] Date of Patent: May 7, 1991

[54] PROCESS FOR PREPARING OPTICALLY ACTIVE 2-OXOIMIDAZOLIDINE DERIVATIVES

[75] Inventors: Kimiaki Hayashi, Suita; Hitoshi Kubota, Ashiya, both of Japan

[73] Assignee: Tanabe Seiyaku Co., Ltd., Osaka, Japan

[21] Appl. No.: 445,060

[22] Filed: Dec. 4, 1989

[30] Foreign Application Priority Data

Dec. 16, 1988 [JP] Japan .................................. 63-318745

[51] Int. Cl.$^5$ .......................................... C07D 233/30
[52] U.S. Cl. .................................................. 548/320
[58] Field of Search ....................................... 548/320

[56] References Cited

U.S. PATENT DOCUMENTS 4,508,727 4/1985 Yoneda et al. ........................ 514/398

FOREIGN PATENT DOCUMENTS 60-58233 12/1985 Japan ................................... 514/398

OTHER PUBLICATIONS

Yoneda et al., Chem. Abstracts, vol. 100, (21), Abst. No. 174,828z, 1984.

Primary Examiner—Mary C. Lee
Assistant Examiner—Joseph K. McKane
Attorney, Agent, or Firm—Browdy and Neimark

[57] ABSTRACT

Disclosed are a process for preparing an optically active 2-oxoimidazolidine derivative of the formula:

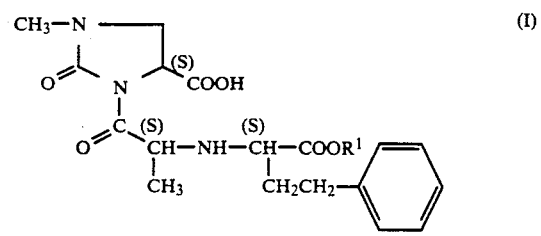

wherein $R^1$ represents hydrogen atom or a lower alkyl group, according to the process described in the specification; and a 3-acyl-2-oxoimidazolidine-4-carboxylin acid ester derivative having (S, R) configuration of the formula:

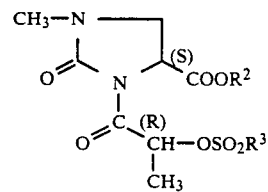

wherein $R^2$ represents a tert-butyl group or a benzyl group, and $R^3$ represents a lower alkyl group or an aryl group.

9 Claims, No Drawings

PROCESS FOR PREPARING OPTICALLY ACTIVE 2-OXOIMIDAZOLIDINE DERIVATIVES

BACKGROUND OF THE INVENTION

This invention relates to a novel process for preparing optically active 2-oxoimidazolidine derivatives useful as pharmaceutical compounds.

This invention also relates to a novel intermediate of said 2-oxoimidazolidine derivative.

2-Oxoimidazolidine derivatives represented by the formula:

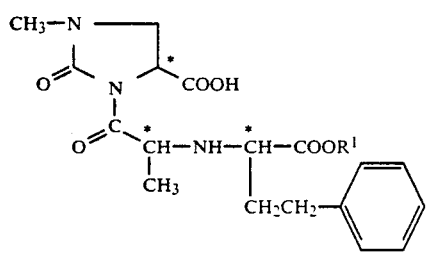

wherein $R^1$ represents hydrogen atom or a lower alkyl group and * represents an asymmetric carbon atom, are pharmaceutical compounds useful as hypotensors having excellent angiotensin converting enzyme (ACE) inhibitory activity.

The 2-oxoimidazolidine derivatives have three asymmetric carbons within the molecule, and their absolute configurations affect greatly the activity, and it has been known in the art that compounds of (S, S, S) configuration in which the absolute configurations of the three asymmetric carbon atoms are all (S) configurations are most preferred (Japanese Patent Publication No. 58233/1985).

As a process for preparing compounds having such (S, S, S) configuration, in the above-mentioned patent specification, there is disclosed a process which comprises (1) reacting a (4S)-1-methyl-2-oxoimidazolidine-4-carboxylic acid ester with 2-bromopropionic acid chloride to form (4S)-1-methyl-3-(2-bromopropionyl)-2-oxoimidazolidine-4-carboxylic acid ester, (2) reacting this product with a (2S)-2-amino-4-phenylbutyric acid ester, then separating the compound of (S, S, S) configuration from the product, and subsequently (3) eliminating the ester residue.

However, according to the above known method, in the condensation reaction of the step (2), the compound of (S, S, S) configuration and the compound of (S, R, S) configuration are formed, and also diastereo-selectivity is exhibited to give the compound of (S, R, S) configuration as the major product. For this reason, there have been involved drawbacks that separation of the compound of (S, S, S) configuration from the compound of (S, R, S) configuration is required for isolation thereof and also that the isolation yield of the (S, S, S) isomer is low.

Also, in the above known method, even when 2-bromopropionic acid chloride may be replaced with a compound of (S) configuration or (R) configuration, racemization and diastereoselectivity occur in the reaction of the step (2) to produce compounds of (S, S, S) configuration and (S, R, S) configuration, and also give the compound of (S, R, S) configuration as the major product, thus involving the same drawbacks as mentioned above.

SUMMARY OF THE INVENTION

The present inventors, in view of the state of the art as described above, made various studies in order to establish a process which can prepare industrially advantageously 2-oxoimidazolidine derivatives of (S, S, S) configuration having potent activity, and consequently found that by use of a reactive derivative at the carboxyl group of (2R)-2-lower alkylsulfonyloxy (or arylsulfonyloxy)propionic acid in place of 2-bromopropionic acid in the above known method, no racemization occurs in the course of the reaction, and also the above (R) configuration is inverted to the (S) configuration in the condensation reaction with the (2S)-2-amino-4-phenylbutyric acid ester to give the desired 2-oxoimidazolidine-4-carboxylic acid derivative having (S, S, S) configuration stereoselectively and at high yield, to accomplish the present invention.

Thus, an object of the present invention is to provide a novel process for preparing 2-oxoimidazolidine derivative of (S, S, S) configuration. Another object of the present invention is to provide a novel intermediate of said 2-oxoimidazolidine derivative.

According to the present invention, the optically active 2-oxoimidazolidine derivative having (S, S, S) configuration of the formula:

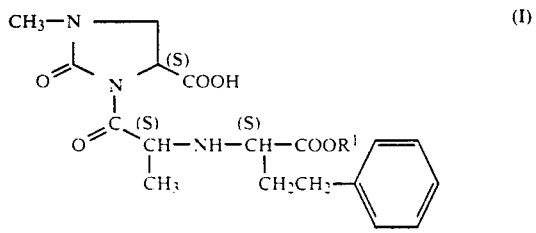

wherein $R^1$ represents hydrogen atom or a lower alkyl group, can be prepared by reacting a 2-oxoimidazolidine-4-carboxylic acid ester derivative having (S) configuration of the formula:

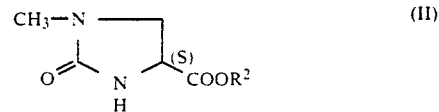

wherein $R^2$ represents a tert-butyl group or a benzyl group, with a reactive derivative at the carboxyl group of a propionic acid compound having (R) configuration of the formula:

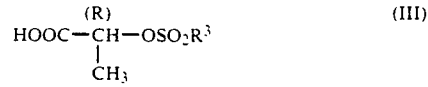

wherein $R^3$ represents a lower alkyl group or an aryl group, to form a 3-acyl-2-oxoimidazolidine-4-carboxylic acid ester derivative having (S, R) configuration of the formula:

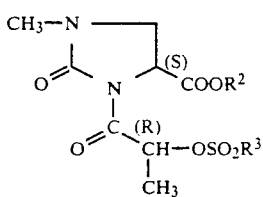

(IV)

wherein R² and R³ have the same meanings as defined above,
and reacting said compound with an amino acid ester derivatives having (S) configuration of the formula:

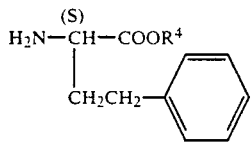

(V)

wherein R⁴ represents a lower alkyl group or a benzyl group,
to form a 2-oxoimidazolidine diester derivative having (S, S, S) configuration of the formula:

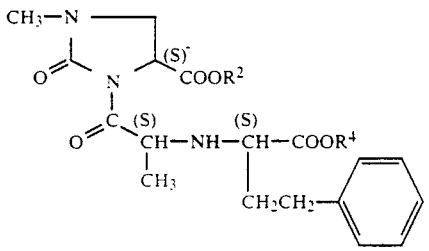

(VI)

wherein R² and R⁴ have the same meanings as defined above,
and subsequently eliminating R² from said compound and also when R⁴ is a benzyl group further eliminating said benzyl group.

DESCRIPTION OF THE PREFERRED EMBODIMENTS

The condensation reaction between the 2-oxoimidazolidine-4-carboxylic acid ester (II) having (S) configuration and the reactive derivative at the carboxyl group of the propionic acid compound (III) having (R) configuration can be preferably practiced in an appropriate solvent in the presence of an acid acceptor. As the group represented by R³ in the compound (III), lower alkyl groups such as methyl, ethyl, etc. and aryl groups such as phenyl, p-methylphenyl, etc. may be included, and as the reactive derivative at the carboxyl group of the compound (III), for example, active ester with N-hydroxysuccinic imide or acid halides such as acid chloride and an acid bromide may be included. As the acid acceptor, for example, potassium t-butoxide, sodium hydroxide, potassium hydroxide, etc. can be preferably used, and as the solvent, tetrahydrofuran, dioxane, dimethylformamide, etc. can be preferably used. This reaction should be preferably practiced under cooling to room temperature.

Thus, the compound (IV) having (S, R) configuration is obtained, and this compound is a novel compound.

The condensation reaction between the compound (IV) having (S, R) configuration obtained as described above and the amino acid ester (V) having (S) configuration should be preferably practiced in an appropriate solvent or without solvent in the presence of an acid acceptor. As the acid acceptor, it is preferable to use, for example, an alkali carbonate such as potassium carbonate, sodium carbonate, or an organic tertiary amine such as triethylamine, tributylamine, N-methylmorpholine, etc., or alternatively, the compound (V) can be used in excess in place of the acid acceptor. As the solvent, for example, dimethyl sulfoxide, hexamethylphosphorylamide, dimethylformamide, etc. can be preferably used.

This reaction proceeds preferably at room temperature to under heating and only the (S, S, S) configuration isomer is produced stereoselectively and at good yield.

Elimination of tert-butyl group and/or benzyl group from the 2-oxoimidazolidine diester derivative (VI) having (S, S, S) configuration thus obtained can be practiced according to conventional methods. For example, elimination of tert-butyl can be practiced preferably by acid treatment, while benzyl group by catalytic reduction.

According to the process of the present invention as described above, only the optically active 2-oxoimidazolidine derivative having (S, S, S) configuration exhibiting potent angiotensin converting enzyme (ACE) inhibitory activity can be prepared stereoselectively and at good yield, and hence the process of the present invention is an industrially very advantageous process.

EXAMPLE 1

(1) To a solution of D-lactic acid O-tosylate, namely (2R)-2-(p-toluenesulfonyloxy)propionic acid (1.15 g) in chloroform (5 ml) was added thionyl chloride (0.69 ml), and the mixture was heated under reflux for 3 hours. After the reaction mixture was concentrated under reduced pressure, chloroform was added to the residue, followed by reconcentration to give an acid chloride (residue A). On the other hand, (4S)-1-methyl-2-oxoimidazolidine-4-carboxylic acid t-butyl ester (1.08 g) was dissolved in tetrahydrofuran (12 ml), and potassium t-butoxide (607 mg) was added thereto under cooling at $-50°$ C. and the mixture was stirred for 20 minutes. To the solution was added a solution of the above acid chloride (residue A) in tetrahydrofuran (2 ml) at the same temperature, followed by stirring for 20 minutes. To the reaction mixture was added a mixed solution of ethyl acetate (6 ml), acetic acid (320 mg) and saturated aqueous sodium chloride (6 ml). The organic layer was taken by separation, washed successively with saturated aqueous sodium chloride, 5 % aqueous potassium carbonate, saturated aqueous sodium chloride, and then dried. Evaporation of the solvent, purification of the residue by silica gel chromatography (chloroform:ethyl acetate=2:1) and crystallization from n-hexane gave t-butyl (4S)-1-methyl-3-[(2R)-2-(p-toluenesulfonyloxy)-propionyl]-2-oxoimidazolidine-4-carboxylate (1.48 g). Yield: 74 %, m.p.: 78°–80° C.
$[\alpha]_D^{25}$: $-3.0°$ (C=1, chloroform).
IR $\nu_{max}^{Nujol}$ (cm⁻¹): 1750, 1735, 1690.
NMR (CDCl₃) δ: 1.46 (9H,s), 1.47 (3H,d,J=7 Hz), 2.41 (3H,s), 2.87 (3H,s), 3.31 (1H,dd,J=4,9 Hz), 3.70 (1H,t,J=9 Hz), 4.50 (1H,dd,J=4,9 Hz), 6.26 (1H,q,J=7 Hz), 7.29, 7.80 (2H each, A₂B₂,J=7 Hz).

(2) To ethyl (2S)-2-amino-4-phenylbutyrate (prepared from 0.86 g of hydrochloride thereof) were added dimethylsulfoxide (1 ml), triethylamine (0.65 ml) and the product of the above (1) (1.0 g), and the mixture was heated under stirring at 80° C. for 24 hours. To the reaction mixture was added saturated aqueous sodium chloride (3 ml), followed by extraction with ethyl acetate. The extract was washed with aqueous sodium chloride, and then dried. Evaporation of the solvent and purification of the residue by silica gel chromatography (chloroform:ethyl acetate=2:1) gave t-butyl (4S)-1-methyl-3-{(2S)-2-[N-((1S)-1-ethoxycarbonyl-3-phenylpropyl)-amino]propionyl}-2-oxoimidazolidine-4-carboxylate (950 mg) as colorless syrup. Yield: 87.8%.

IR $\nu_{max}^{Nujol}$(cm$^{-1}$): 3300, 1730, 1680.

MS m/e: 461 (M+).

Maleic acid salt of this product:
m.p.: 122°-124° C. (decompd.).
$[\alpha]_D^{25}$: −58.2° (C=1, ethanol).

(3) To this product (500 mg) was added 15% hydrochloric acid-dioxane solution (20 ml), and the mixture was stirred overnight. The crystals precipitated were collected by filtration, washed with ether to give (4S)-1-methyl-3-{(2S)-2-[N-((1S)-1-ethoxycarbonyl-3-phenylpropyl)amino]-propionyl}-2-oxsoimidazolidine-4-carboxylic acid hydrochloride (455 mg). Yield: 95%, m.p.: 214°-216° C. (decompd.).
$[\alpha]_D^{25}$: −64.1° (C=1, ethanol).
IR $\nu_{max}^{Nujol}$(cm$^{-1}$): 1720, 1695, 1640, 1610.
MS m/e: 405 (M+).

EXAMPLE 2

(1) To a solution of D-lactic acid O-tosylate (4.59 g) in tetrahydrofuran (50 ml) was added N-hydroxysuccinic imide (2.21 g). Then, under cooling, dicyclohexylcarbodiimide (3.96 g) was added, and the mixture was stirred at room temperature overnight. Insolubles were filtered off and the solvent was evaporated under reduced pressure to obtain an active ester (residue B) as oily substance. On the other hand, t-butyl (4S)-1-methyl-2-oxoimidazolidine4-carboxylate (4.14 g) was dissolved in tetrahydrofuran (37 ml), and under cooling at −50° C., potassium t-butoxide (2.32 g) was added, followed by stirring for 20 minutes. Further, under cooling at −50° C., a solution of the above active ester (residue B) in tetrahydrofuran (10 ml) was added, and the mixture was stirred for 15 minutes. To the reaction mixture was added a mixed solution of ethyl acetate (24 ml), acetic acid (1.24 g) and saturated aqueous sodium chloride (24 ml). The organic layer was separated, successively washed with saturated aqueous sodium chloride, 5 % aqueous potassium carbonate and saturated aqueous sodium chloride and then dried. Evaporation of the solvent, purification of the residue by silica gel chromatography (toluene:ethyl acetate=2:1) and crystallization from n-hexane gave t-butyl (4S)-1-methyl-3-[(2R)-2-(p-toluenesulfonyloxy)propionyl]-2-oxoimidazolidine-4-carboxylate (5.17 g). Yield: 64.5%.

The physicochemical properties of this product are identical with those of the product obtained in Example 1- (1).

EXAMPLE 3

(1) D-lactic acid O-mesylate, namely (2R)-2-(methanesulfonyloxy)propionic acid (2.5 g) and t-butyl (4S)-1-methyl-2-oxoimidazolidine-4-carboxylate (3.42 g) were treated similarly as in Example 1 - (1), and the crude product was purified by silica gel chromatography (chloroform:ethyl acetate=1:2) and crystallized from n-hexane to give t-butyl (4S)-1-methyl-3-[(2R)-2-(methanesulfonyloxy)-propionyl]-2-oxoimidazolidine-4carboxylate (3.95 g). Yield: 75.8%., m.p.: 97°-100° C.
$[\alpha]_D^{25}$: −3.2° (C=2, chloroform).
IR $\nu_{max}^{Nujol}$(cm$^{-1}$); 1740, 1700.
NMR (CDCl$_3$) δ: 1.46 (9H,s), 1.61 (3H,d,J=7 Hz) 2.89 (3H,s), 3.02 (3H,s), 3.35 (1H,dd,J=4,10 Hz), 3.74(1H,t,J=10 Hz), 4.58 (1H,dd,J=4,10 Hz), 6.35 (1H,q,J=7 Hz).

(2) This product (1 g) and ethyl (2S)-2-amino-4-phenylbutyrate (0.89 g) were treated similarly as in Example 1 - (2) to obtain t-butyl (4S)-1-methyl-3-{(2S)-2-[N-((1S)-1-ethoxycarbonyl -3-phenylpropyl)amino]-propionyl}-2-oxoimidazolidine-4-carboxylate (1.2 g) as syrup. Yield: 91.1 %.

The physicochemical properties of this product are identical with those of the product obtained in Example 1 - (2).

EXAMPLE 4

(1) D-lactic acid O-mesylate (1.97 g) and benzyl (4S)-1-methyl-2-oxoimidazolidine-4-carboxylate (2.27 g) were treated similarly as in Example 1 - (1), and the crude product was purified by silica gel chromatography (ethyl acetate) and crystallized from isopropyl ether to give benzyl (4S)-1-methyl-3-[(2R)-2-(methanesulfonyloxy)propionyl]-2-oxoimidazolidine-4-carboxylate (3.01 g). Yield: 80.8%, m.p.: 98°-102° C.
$[\alpha]_D^{25}$: −5.0° (C=2, chloroform).
IR $\nu_{max}^{Nujol}$(cm$^{-1}$); 1765, 1730, 1715, 1700.
NMR (CDCl$_3$) δ: 1.61 (3H,d,J=7 Hz), 2.86 (3H,s), 2.91 (3H,s), 3.36 (1H,dd,J=4,10 Hz), 3.73 (1H,t,J=10 Hz), 4.77 (1H,dd,J=4,10 Hz), 5.20 (2H,s), 6.35 (1H,q,J=7 Hz), 7.33 (5H,s).
MS m/z: 384 (M−).

(2) This product (1 g) and ethyl (2S)-2-amino-4-phenylbutyrate hydrochloride (950 mg) were treated similarly as in Example 1 - (2), and the crude product was purified by silica gel chromatography to give benzyl (4S)-1-methyl-3-{(2S)-2-[N-{(1S)-1-ethoxycarbonyl-3-phenylpropyl)amino]propionyl}-2-oxoimidazolidine-4-carboxylate (850 mg) as colorless syrup. Yield: 65.9%.

Maleic acid salt of this product:
m.p. 84°-86° C. (recrystallized from ethyl acetate isopropyl ether).
$[\alpha]_D^{25}$: −49.8 (C=1, ethanol).

(3) This product (1 g) was dissolved in ethanol (30 ml), and catalytically reduced with addition of 10% palladium carbon (200 mg) under normal temperature and normal pressure for 3 hours. The catalyst was filtered off, and the solvent was evaporated. To the crystalline residue was added ether, and the product was collected by filtration to give (4S)-1-methyl-3-((2S)-2-[N-{(1S)-1-ethoxycarbonyl-3-phenylpropyl)amino]propionyl}-2-oxoimidazolidine-4-carboxylic acid (780 mg). Yield: 95.4%, m.p.: 140° C.
$[\alpha]_D^{24}$: −71.9° (C=0.5, ethanol).

EXAMPLE 5

(1) t-Butyl (4S)-1-methyl-3-[(2R)-2-(p-toluenesulfonyloxy)propionyl]-2-oxoimidazolidine-4-carboxylate (1 g) obtained in Example 1 - (1) and benzyl (2S)-2-amino-4-phenylbutyrate (1.55 g) were treated similarly as in Example 1 - (2) to give t-butyl (4S)-1-methyl-3-{(2S)-2-[N-((1S)-1-benzyloxycarbonyl-3-phenylpropyl)amino]propionyl}-2-oxoimidazolidine-4-carboxylate (1.01 g) as colorless syrup. Yield: 82.3%.

Maleic acid salt of this product:

m.p.: 108°–112° C.

[α]$_D^{25}$: −57.4° (C=1, ethanol).

(2) This product (1.05 g) was dissolved in methanol (30 ml), and catalytically reduced with addition of 10% palladium-carbon (300 mg) under normal temperature and normal pressure for 3 hours. The catalyst was filtered off, and the filtrate was concentrated under reduced pressure. The crystals precipitated were collected by filtration, and washed with ether. Subsequently, this product was suspended in dioxane (10 ml), and 25 % hydrochloric acid-dioxane solution (10 ml) was added thereto, followed by stirring at room temperature overnight. The precipitated crystals were collected by filtration, dissolved in water and adjusted to pH 6 with sodium hydrogen carbonate. The precipitated crystals were collected by filtration, washed with water and dried to give (4S)-1-methyl-3-{(2S)-2-[N-{(1S)-1-carboxy-3-phenylpropyl)amino]propionyl}-2-oxoimidazolidine-4-carboxylic acid (664 mg). Yield: 88 %.

m.p.: 240° C. (decompd.)

[α]$_D^{25}$: −89° (C=1, 5% aqueous sodium hydrogen carbonate).

EXAMPLE 6

(1) To a solution of D-lactic acid O-tosylate (2g) in chloroform (20 ml) was added thionyl chloride (2.39 ml), and the mixture was heated under reflux for 3 hours. The reaction mixture was concentrated under reduced pressure, then reconcentrated with addition of chloroform to obtain an acid chloride (residue C). On the other hand, benzyl (4S)-1-methyl-2-oxoimidazolidine-4-carboxylate (2.21 g) was dissolved in tetrahydrofuran (25 ml), and under cooling at −50° C., potassium t-butoxide (1.06 g) was added under nitrogen gas stream, followed by stirring for 20 minutes. To this solution was added at the same temperature a solution of the above acid chloride (residue C) in tetrahydrofuran (4 ml), followed by stirring for 20 minutes. To the reaction mixture were added a mixed solution of ethyl acetate (15 ml), acetic acid (0.57 g) and saturated aqueous sodium chloride (15 ml). The organic layer was taken by separation, successively washed with saturated aqueous sodium chloride, aqueous 5 % potassium carbonate, saturated aqueous sodium chloride, and then dried. Evaporation of the solvent and recrystallization of the residue from ethyl acetate gave benzyl (4S)-1-methyl-3-[(2R)-2-(p-toluenesulfonyloxy)-propionyl] -2-oxoimidazolidine-4-carboxylate (3.1 g).

Yield: 82.8%, m.p.: 153°–155° C.

[α]$_D^{25}$: +2.5° (C=2, chloroform).

IR$\nu_{max}^{Nujol}$(cm$^{-1}$): 1740, 1730, 1695.

NMR (CDCl$_3$) δ: 1.48 (3H,d,J=7 Hz), 2.40 (3H,s), 2.82 (3H,s), 3.28 (1H,dd,J=4,10 Hz), 3.68 (1H,t,J=10 Hz), 4.66 (1H,dd,J=4,10 Hz), 5.10, 5.26 (1H×2,AB,J=12 Hz), 6.24(1H,q,J=7 Hz), 7.32 (5H,s), 7.25, 7.77 (2H each,A$_2$B$_2$, J=8 Hz).

MS m/z: 460 (M$^+$)

(2) This product (1 g) and benzyl (2S)-2-amino-4-phenylbutyrate (1.44 g) were treated similarly as in Example 1 -(2), and the crude product was purified by silica gel chromatography (chloroform:ethyl acetate=4:1) to give benzyl ((4S)-1-methyl-3-{(2S)-2-[N-((1S)-1-benzyloxycarbonyl-3-phenylpropyl)amino]propionyl}-2-oxoimidazolidine-4-carboxylate (0.82 g) as colorless syrup. Yield: 67.7%.

Maleic acid salt of this product:
m.p.: 111°–115° C. (decompd.).

[α $_D^{25}$: −51.6° (C=1, ethanol).

(3) This product (0.5 g) was dissolved in methanol (50 ml) and catalytically reduced with addition of palladium black (50 mg) under normal temperature and normal pressure for 3 hours. The catalyst was filtered off, and the solvent was evaporated. To the crystalline residue was added ether, and the product was separated by filtration to give (4S)-1-methyl-3-{(2S)-2-[N-((1S)-1-carboxy-3-phenylpropyl)amino]propionyl}-2-oxoimidazolidine-4-carboxylic acid. The physicochemical properties of this product are identical with those of the product obtained in Example 5 - (2).

We claim:

1. A process for preparing an optically active 2-oxoimidazolidine derivative of the formula:

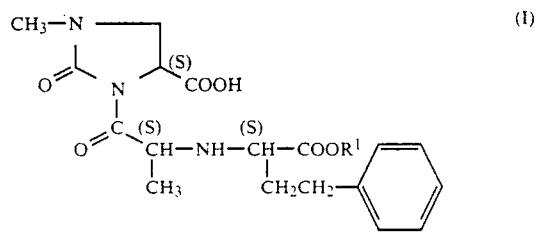

wherein R$^1$ represents hydrogen atom or a lower alkyl group, which comprises reacting a 2-oxoimidazolidine-4-carboxylic acid ester derivative having (S) configuration of the formula:

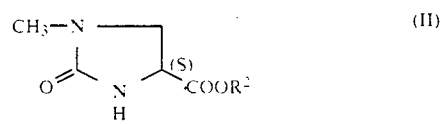

wherein R$^2$ represents a tert-butyl group or a benzyl group, with a reactive derivative at the carboxyl group of a propionic acid compound having (R) configuration of the formula:

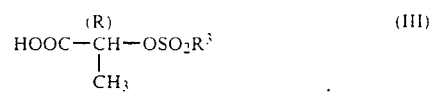

wherein R$^3$ represents a lower alkyl group or an aryl group to form a 3-acyl-2-oxoimidazolidine-4-carboxylic acid ester derivative having (S, R) configuration of the formula:

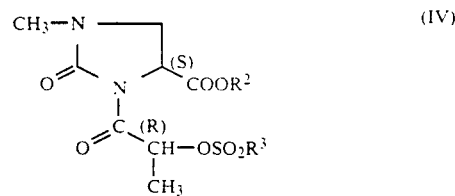

wherein R$^2$ and R$^3$ have the same meanings as defined above, and reacting, in the presence of an organic tertiary amine, said compound (IV) with an amino acid ester having (S) configuration of the formula:

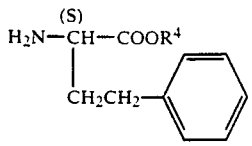 (V)

wherein R⁴ represents a lower alkyl group or a benzyl group, to form a 2-oxoimidazolidine diester derivative having (S, S, S) configuration of the formula:

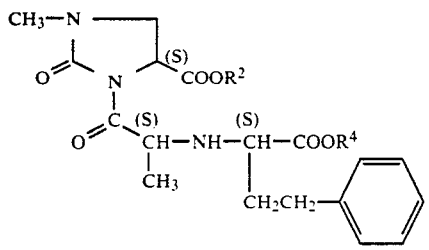 (VI)

wherein R² and R⁴ have the same meanings as defined above, and subsequently eliminating R² from said compound and also when R⁴ is a benzyl group further eliminating said benzyl group.

2. The process according to claim 1, wherein R³ in said compound (III) is a methyl group, an ethyl group, a phenyl group or p-methylphenyl group.

3. The process according to claim 1, wherein said reactive derivative at the carboxyl group of the compound (III) is an active ester with N-hydroxysuccinic imide, an acid chloride or an acid bromide.

4. The process according to claim 1, wherein said condensation reaction of the compound (II) and the compound (III) is practiced in the presence of an acid acceptor selected from potassium t-butoxide, sodium hydroxide or potassium hydroxide.

5. The process according to claim 1, wherein said condensation reaction of the compound (II) and the compound (III) is practiced in the presence of a solvent selected from tetrahydrofuran, dioxane or dimethylformamide.

6. The process according to claim 1, wherein said condensation reaction of the compound (II) and the compound (III) is practiced under cooling to room temperature.

7. The process according to claim 1, wherein said organic tertiary amine is triethylamine, tributylamine or N-methylmorpholine.

8. The process according to claim 1, wherein said condensation reaction of the compound (IV) and the compound (V) is practiced in the presence of a solvent selected from dimethyl sulfoxide, hexamethylphosphorylamide or dimethylformamide.

9. The process according to claim 1, wherein said condensation reaction of the compound (IV) and the compound (V) is practiced at room temperature to under heating.

* * * * *